US011298149B2

(12) United States Patent
Tada et al.

(10) Patent No.: US 11,298,149 B2
(45) Date of Patent: Apr. 12, 2022

(54) MEDICAL DEVICE

(71) Applicant: TERUMO KABUSHIKI KAISHA, Tokyo (JP)

(72) Inventors: Yuichi Tada, Tokyo (JP); Mizuho Hirao, Sagamihara (JP)

(73) Assignee: TERUMO KABUSHIKI KAISHA, Tokyo (JP)

( * ) Notice: Subject to any disclaimer, the term of this patent is extended or adjusted under 35 U.S.C. 154(b) by 144 days.

(21) Appl. No.: 16/578,603

(22) Filed: Sep. 23, 2019

(65) Prior Publication Data

US 2020/0015843 A1 Jan. 16, 2020

Related U.S. Application Data

(63) Continuation of application No. PCT/JP2018/010881, filed on Mar. 19, 2018.

(30) Foreign Application Priority Data

Mar. 24, 2017 (JP) .............................. JP2017-059455

(51) Int. Cl.
*A61B 17/3207* (2006.01)
*A61B 17/22* (2006.01)
*A61B 17/00* (2006.01)

(52) U.S. Cl.
CPC .............. *A61B 17/320758* (2013.01); *A61B 2017/00778* (2013.01); *A61B 2017/22045* (2013.01); *A61B 2017/22079* (2013.01)

(58) Field of Classification Search
CPC .... A61B 17/320758; A61B 17/320783; A61B 17/320725
See application file for complete search history.

(56) References Cited

U.S. PATENT DOCUMENTS 4,979,939 A 12/1990 Shiber
5,041,082 A 8/1991 Shiber
(Continued)

FOREIGN PATENT DOCUMENTS

CN 103200886 A 7/2013
CN 103386163 A 11/2013
(Continued)

OTHER PUBLICATIONS

International Search Report (with English translation) and Written Opinion issued in corresponding International Patent Application No. PCT/ JP2018/010881, 7 pages (dated Jun. 5, 2018).
(Continued)

*Primary Examiner* — Tuan V Nguyen
(74) *Attorney, Agent, or Firm* — Buchanan Ingersoll & Rooney PC

(57) ABSTRACT

A medical device is disclosed that can help prevent an object existing in a body lumen from clogging a lumen of an elongated member. The medical device including an elongated member having a lumen extending in an axial direction; an insertion member inserted in the lumen of the elongated member on a distal side of the lumen; and a breaking member fixed on an inner surface of the elongated member such that a gap is formed between the insertion member and the breaking member in the lumen of the elongated member on the distal side, and wherein the breaking member exerts a shearing force to the object by rotating relative to the insertion member while the object is between the insertion member and the breaking member.

20 Claims, 15 Drawing Sheets

(56) References Cited

U.S. PATENT DOCUMENTS

| | | | | |
|---|---|---|---|---|
| 2008/0045986 A1* | 2/2008 | To | .................. | A61B 17/320708 |
| | | | | 606/159 |
| 2009/0018565 A1 | 1/2009 | To et al. | | |
| 2009/0234378 A1 | 9/2009 | Escudero et al. | | |
| 2012/0109171 A1* | 5/2012 | Zeroni | ........... | A61B 17/320758 |
| | | | | 606/159 |

FOREIGN PATENT DOCUMENTS

| | | | |
|---|---|---|---|
| JP | H01131653 A | 5/1989 | |
| JP | H02104371 A | 4/1990 | |
| JP | 2010532211 A | 10/2010 | |
| JP | 2014533147 A | 12/2014 | |

OTHER PUBLICATIONS

Office Action (First Office Action) dated Dec. 28, 2021, by the State Intellectual Property Office of People's Republic of China in corresponding Chinese Patent Application No. 201880019919.1 and an English Translation of the Office Action. (14 pages).

* cited by examiner

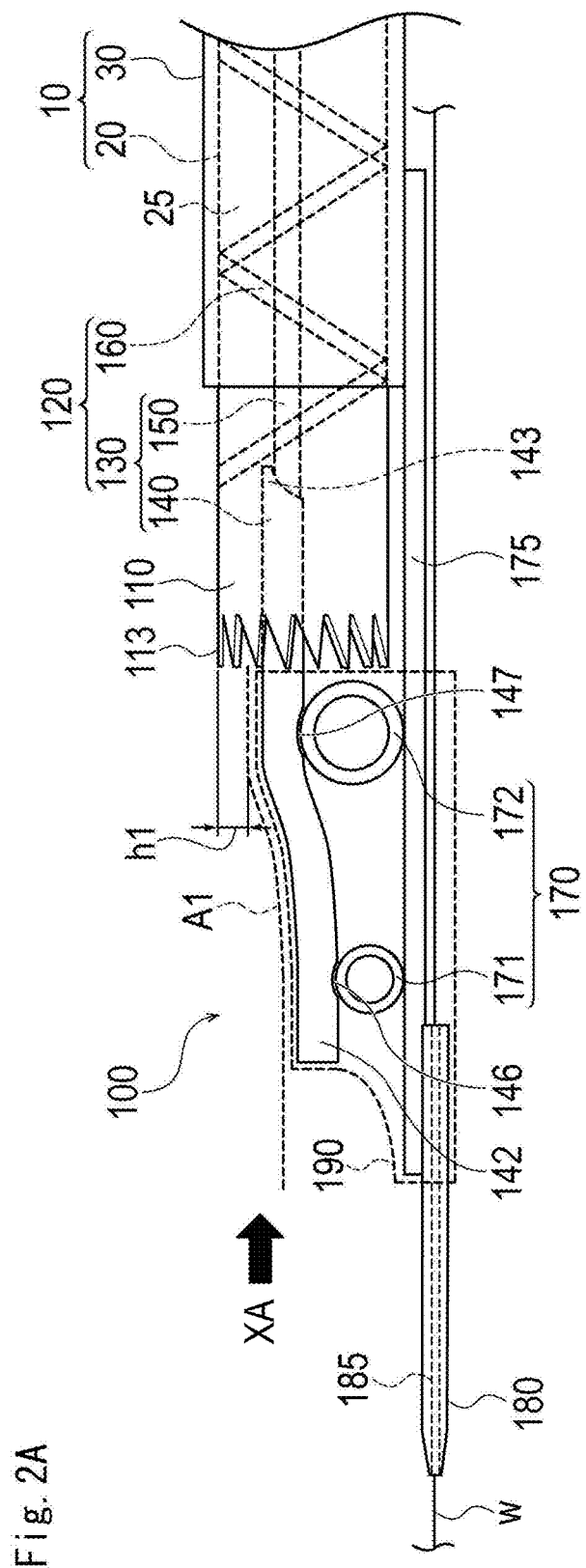

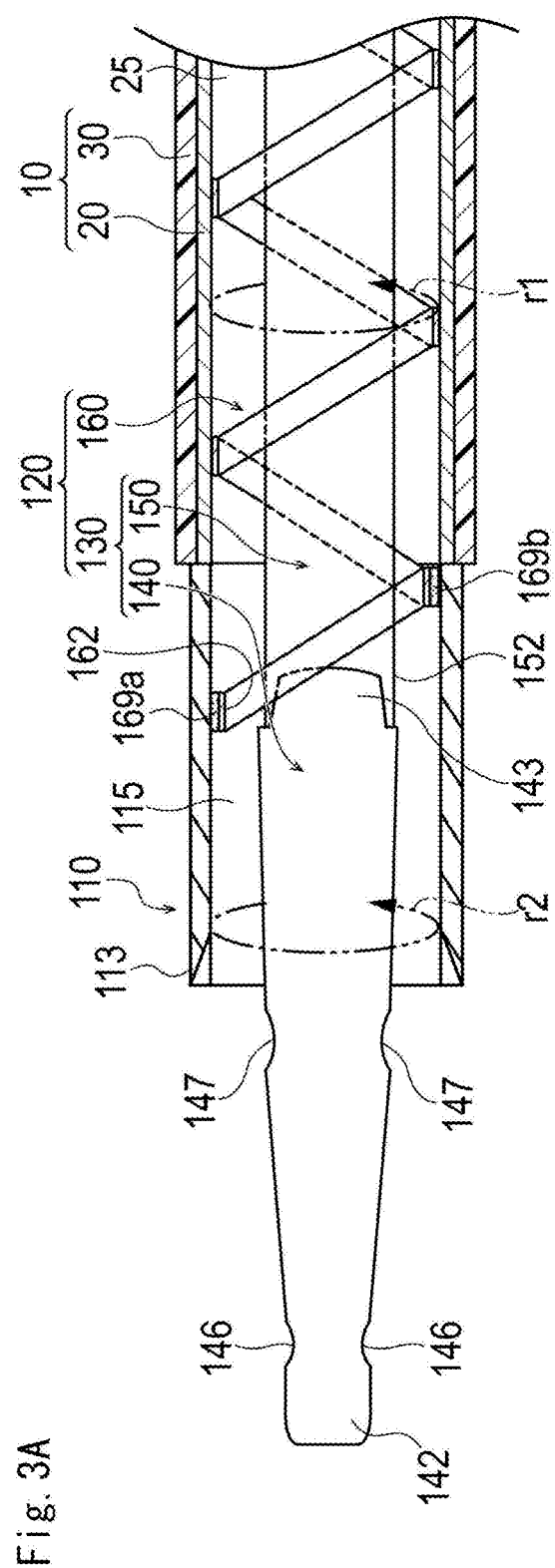

MEDICAL DEVICE

CROSS-REFERENCES TO RELATED APPLICATIONS

This application is a continuation of International Application No. PCT/JP2018/010881 filed on Mar. 19, 2018, which claims priority to Japanese Application No. 2017-059455 filed on Mar. 24, 2017, the entire content of both of which is incorporated herein by reference.

FIELD OF THE DISCLOSURE

The present disclosure relates to a medical device.

BACKGROUND DISCUSSION

As a method of treating a stenosed site formed in a blood vessel such as a coronary artery, a procedure in which a balloon catheter is used or a stent placement technique is performed. However, a long-term treatment effect may not be obtained by widening a vascular lumen by means of a balloon, and the placement of a stent can cause of new stenosis. For example, in a complex lesion, such as a case where plaque in a stenosed site is calcified and hardened or a case where a stenosed site is generated in a bifurcated portion of a blood vessel, a sufficient treatment effect cannot be obtained in some cases simply by performing a procedure in which a balloon catheter or stent is used. For this reason, as a procedure contributing to the extension of a blood vessel patency period or the improvement in complex lesion treatment results, an atherectomy that removes an object which is a cause of stenosis, such as plaque, a calcified lesion, and a thrombus, from a human body has attracted attention (see JP-T-2014-533147).

In a case of performing a procedure in a body lumen such as a blood vessel, it can be difficult to transport an object existing in the blood vessel (for example, debris or a floating thrombus generated by a procedure with respect to a stenosed site).

For example, in a case of performing the transporting of the object (object to be transported) by using a medical device such as a catheter in which a lumen is formed, an aspiration device for applying an aspiration pressure to the lumen can be used. However, since a relatively large pressure loss can occur in a lumen of a relatively long catheter, it can be difficult to apply a sufficient aspiration pressure to a distal portion of the catheter even in a case where the aspiration device is used. In addition, even when the object to be transported can be flowed into the lumen, the object to be transported cannot be transported to a proximal side of the catheter depending on a size of the object to be transported, and thus there is a possibility that clogging occurs in the vicinity of the distal portion of the catheter due to the object to be transported.

SUMMARY

A medical device is disclosed that can prevent an object existing in a body lumen from clogging a lumen of an elongated member.

According to an aspect of the present disclosure, a medical device is disclosed for transporting an object that exists in a body lumen. The medical device can include an elongated member in which a lumen extending in an axial direction is formed, an insertion member of which at least a part is inserted in the lumen of the elongated member on a distal side, and a breaking member that is disposed on an inner surface of the elongated member such that a gap is formed between the insertion member and the breaking member in the lumen of the elongated member on the distal side, and exerts a shearing force to an object, which is a transporting target, by rotating relative to the insertion member in a state where the object is sandwiched between the insertion member and the breaking member.

With the object, which is the transporting target, sandwiched in the gap formed between the breaking member and the insertion member, the medical device according to the present disclosure exerts a shearing force to the object when the breaking member rotates relative to the insertion member. For this reason, the medical device can help prevent the object, which is the transporting target, from clogging the lumen of the elongated member.

In accordance with an aspect, a medical device is disclosed for transporting an object that exists in a body lumen, the medical device comprising: an elongated member having a lumen extending in an axial direction; an insertion member inserted in the lumen of the elongated member on a distal side of the lumen; and a breaking member fixed on an inner surface of the elongated member such that a gap is formed between the insertion member and the breaking member in the lumen of the elongated member on the distal side, and wherein the breaking member exerts a shearing force to the object by rotating relative to the insertion member while the object is between the insertion member and the breaking member.

In accordance with another aspect, a medical device is disclosed for transporting an object that exists in a body lumen, the medical device comprising: an elongated member having a lumen extending in an axial direction; a rotating body that rotates along with rotation of the elongated member on a distal portion of the elongated member; an insertion member partially inserted in the lumen of the elongated member on a distal side of the lumen, the insertion member being configured in a non-rotational state such that the insertion member does not rotate in conjunction with the rotation of the elongated member; and a breaking member fixed on an inner surface of the elongated member and which forms a gap between the insertion member and the breaking member in the lumen of the elongated member on the distal side, and wherein the breaking member exerts a shearing force to the object by rotating relative to the insertion member while the object is between the insertion member and the breaking member, the breaking member being fixed to the elongated member and/or the rotating body, and wherein the breaking member is configured to rotate along with the rotation of the elongated member.

In accordance with an aspect, a method is disclosed for exerting a shearing force to an object from a stenosed site in a body lumen, the method comprising: inserting a medical device into the body lumen, the medical device including an elongated member having a lumen extending in an axial direction, an insertion member inserted in the lumen of the elongated member on a distal side of the lumen, and a breaking member fixed on an inner surface of the elongated member such that a gap is formed between the insertion member and the breaking member in the lumen of the elongated member on the distal side; and exerting a shearing force to the object by rotating the breaking member relative to the insertion member while the object is in the gap between the insertion member and the breaking member in the lumen of the elongated member on the distal side.

BRIEF DESCRIPTION OF THE DRAWINGS

FIG. 2A is an enlarged side view of a distal portion of the medical device according to the embodiment.

FIG. 3A is a simplified cross-sectional view of a configuration of the distal portion of the medical device according to the embodiment.

DETAILED DESCRIPTION

Figure 1:
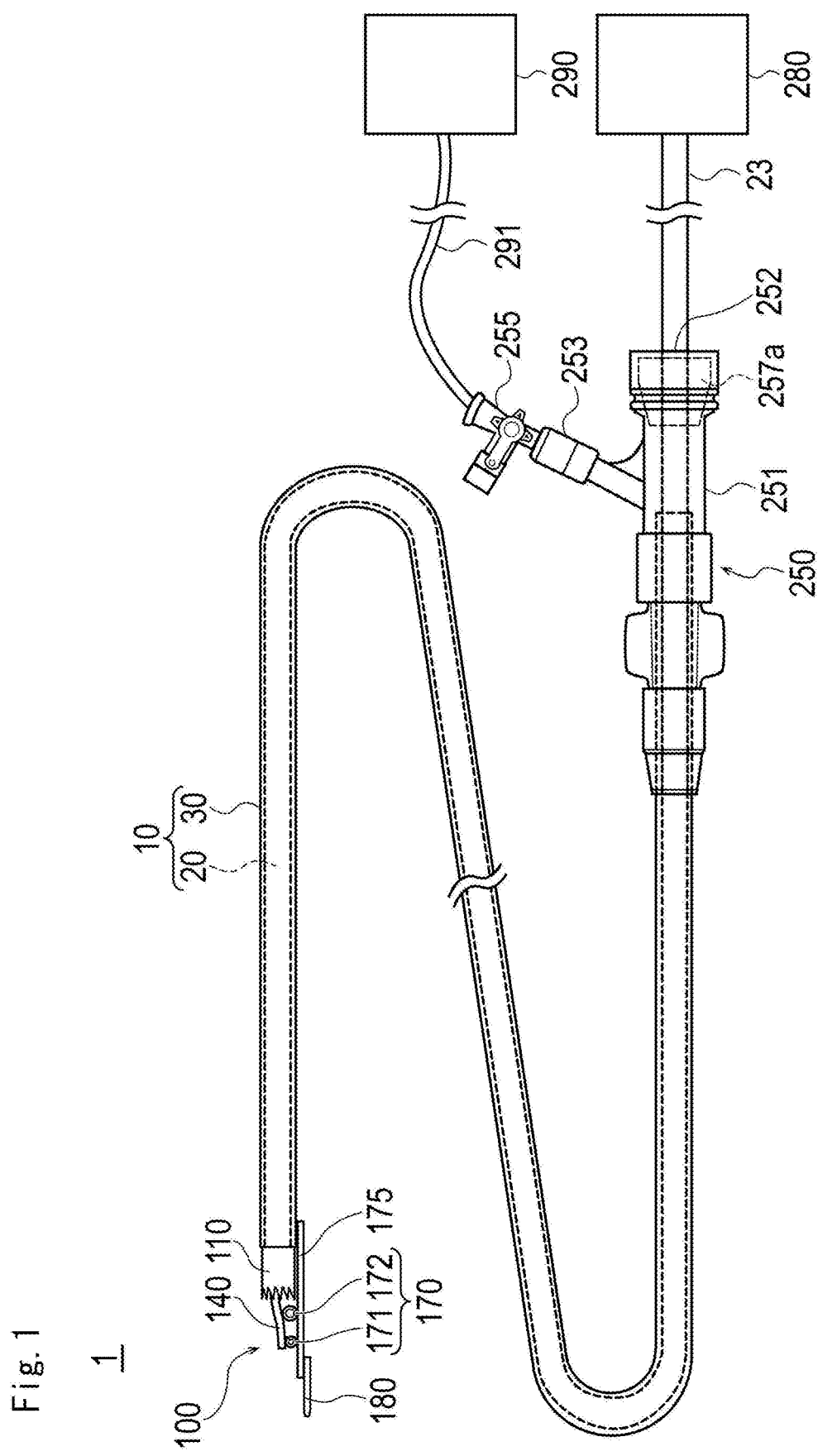
FIG. 1 is a view illustrating a medical device according to an embodiment.

Hereinafter, an embodiment of the present disclosure will be described with reference to the drawings. Note that a dimensional ratio in the drawings is exaggerated for convenience of description, and is different from an actual ratio in some cases.

FIGS. 1 to 7B are views for describing a configuration of each portion of a medical device 1 according to the embodiment, and FIGS. 8 to 10C are views for describing action of the medical device 1.

Figure 8:
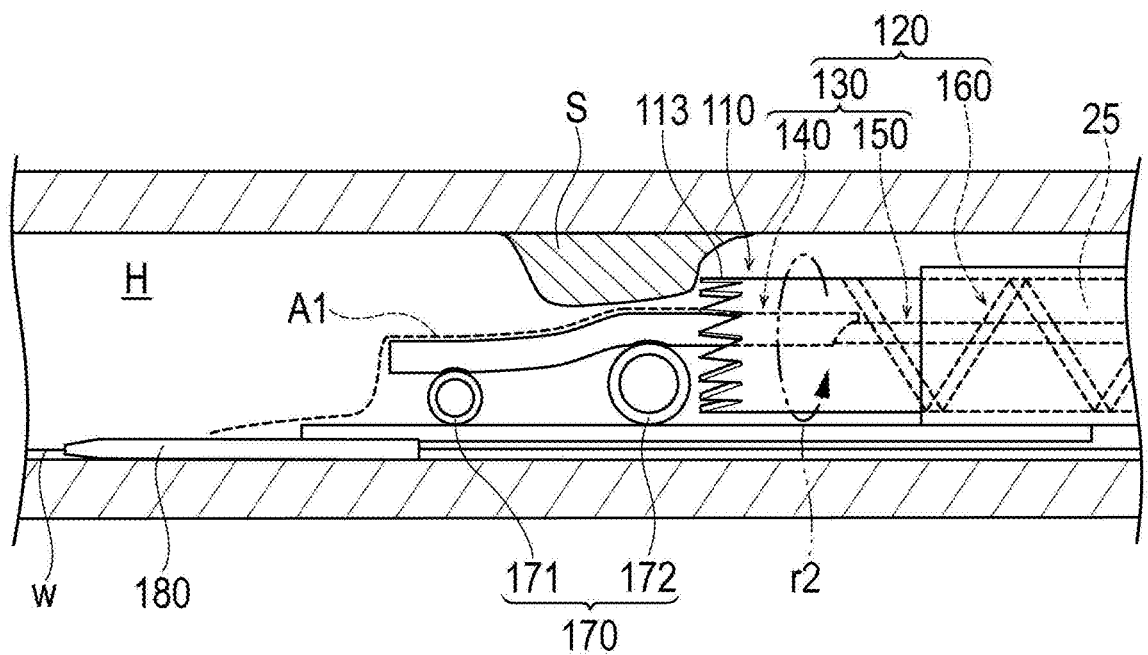
FIG. 8 is a cross-sectional view schematically illustrating a usage example of the medical device according to the embodiment.

As illustrated in FIG. 8, the medical device 1 according to the embodiment is configured as a medical jig that can be used in a procedure of cutting an object such as a stenosed site S or an obstructive part formed in a blood vessel H, which is a body lumen.

To outline with reference to FIG. 1, the medical device 1 has a long sheath 10 that can be introduced into a living body, a distal structure 100 disposed on a distal side of the sheath 10, and a hand operation unit 250 disposed on a proximal side of an elongated member 20.

The distal structure 100 will be described.

Figure 2B:
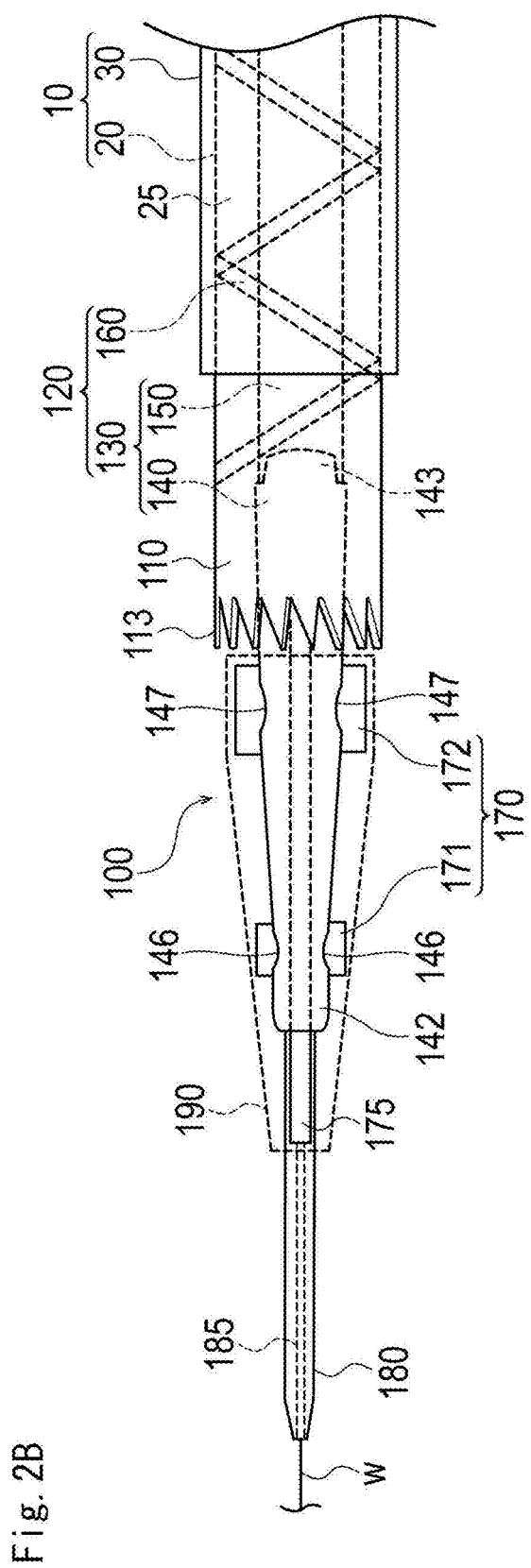
FIG. 2B is an enlarged plan view of the distal portion of the medical device according to the embodiment.
Figure 3B:
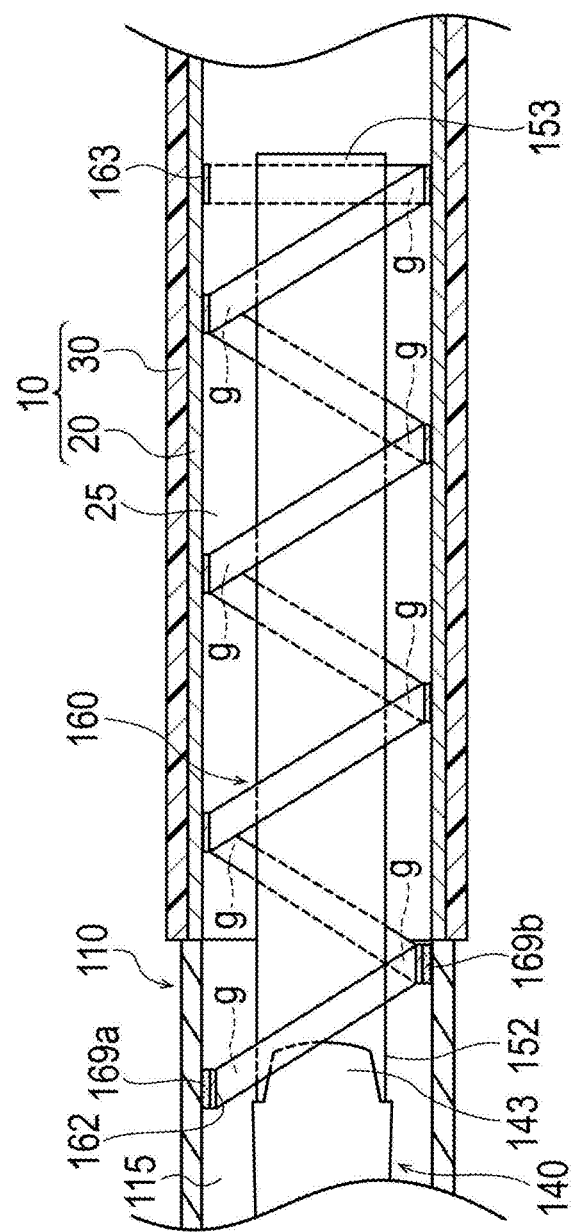
FIG. 3B is a simplified cross-sectional view of the configuration of the distal portion of the medical device according to the embodiment.

FIG. 2A is a side view of a vicinity of a distal portion of the sheath 10, and FIG. 2B is a plan view of the vicinity of the distal portion of the sheath 10. FIGS. 3A and 3B illustrate an enlarged cross section (longitudinal cross section along an axial direction) of the vicinity of the distal portion of the sheath 10. Note that the illustration of some members (i.e., a supporting unit 170, a connection member 175, a guide wire insertion portion 180, and a covering member 190) is omitted in FIGS. 3A and 3B.

In the disclosure, a side of the medical device 1, which is inserted into the blood vessel H, will be referred to as a distal side, and a side where the hand operation unit 250 is disposed will be referred to as a proximal side. In addition, an extending direction of the sheath 10 (a right-and-left direction shown in FIGS. 3A and 3B) will be referred to as the axial direction.

As illustrated in FIGS. 2A and 2B, the distal structure 100 has a rotating body 110 disposed on the distal portion of the sheath 10 and a transporting unit 120 that performs breaking (severing) and transporting of an object (for example, debris D or a floating thrombus which is generated through a procedure with respect to the stenosed site S), which is a transporting target, in a lumen 25 of the sheath 10 (the lumen 25 of the elongated member 20).

As illustrated in FIG. 3A, the rotating body 110 has a hollow shape including a lumen 115 extending in the axial direction. In addition, the rotating body 110 has a cutting unit 113 that applies a cutting force to the stenosed site S. An opening portion that communicates with the lumen 115 is formed in each of a distal portion of the rotating body 110 and a proximal portion of the rotating body 110.

In accordance with an exemplary embodiment, the cutting unit 113 of the rotating body 110 can be formed by an edge surface in a shape, for example, that is notched unevenly to the distal side (saw shape). The cutting unit 113 formed by the saw-shaped edge surface can finely break the stenosed site S, and can perform cutting of the stenosed site S with relatively high efficiency.

Note that a shape, a thickness, a length, and a material for the cutting unit 113 are not particularly limited insofar as it is possible to apply a cutting force to the stenosed site S. For example, it is possible to configure the cutting unit 113 with a known trepanning edge surface (an annular edge surface having a thickness decreasing to the distal side) in the medical field. In a case where the cutting unit 113 is formed by the trepanning edge surface, it is possible to allow the rotating body 110 to relatively smoothly enter the stenosed site S. In addition, in a case where the stenosed site S, for example, is a soft tissue, it is possible to perform cutting of the stenosed site S with relative high efficiency.

In accordance with an exemplary embodiment, the rotating body 110 can be made from, for example, a metal material, a resin material, or ceramics with biocompatibility. For example, stainless steel, nickel titanium (titanium alloy), tungsten, cobalt chromium, titanium, and tungsten carbide can be used as the metal material. Surface treatment, such as nitriding, may be performed on a surface of each of the metal materials so that the material to be used can have a surface with improved hardness than that of the base material. In addition, the cutting unit 113 may be formed by, for example, a multi-layered structure obtained by disposing the same type or different types of metals in multiple layers. For example, ABS (acrylonitrile, butadiene, and a styrene copolymer synthetic resin), polyethylene, polypropylene, nylon, PEEK, polycarbonate, acryl, polyacetal, modified polyphenylene ether, acrylonitrile styrene, and a resin having improved strength by adding an additive such as glass fiber to the resin materials can be used as the resin material.

As illustrated in FIGS. 3A and 3B, the transporting unit 120 has an insertion member 130 that is inserted in the lumen 115 of the rotating body 110 and the lumen 25 of the sheath 10 and a breaking member 160 disposed around the insertion member 130.

In accordance with an exemplary embodiment, the insertion member 130 has a distal member 140, which forms a distal portion of the insertion member 130 and a proximal member 150, which forms a proximal portion of the insertion member 130.

As illustrated in FIG. 3A, a distal portion 142 of the distal member 140 protrudes from a distal end of the rotating body 110. In addition, a proximal portion 143 of the distal member 140 is disposed in the lumen 115 of the rotating body 110.

As illustrated in FIG. 3A, a distal portion 152 of the proximal member 150 can be fixed to the proximal portion 143 of the distal member 140. In addition, as illustrated in FIG. 3B, a proximal portion 153 of the proximal member 150 is disposed in the lumen 25 of the sheath 10. The proximal portion 153 of the proximal member 150 is disposed at a position spaced apart from the rotating body 110 to the proximal side by a predetermined distance.

As illustrated in FIG. 3B, a distal portion 162 of the breaking member 160 is disposed in the lumen 115 of the rotating body 110. The distal portion 162 of the breaking member 160 is disposed at a position of overlapping the proximal portion 143 of the distal member 140 in the axial direction (vicinity of the proximal portion 143).

A proximal portion 163 of the breaking member 160 is disposed at a position spaced apart from the rotating body 110 to the proximal side by a predetermined distance. The proximal portion 163 of the breaking member 160 is disposed at a position of overlapping the proximal portion 153 of the proximal member 150 in the axial direction (vicinity of the proximal portion 153).

As illustrated in FIGS. 3A and 3B, the distal portion 162 of the breaking member 160 can be fixed to an inner wall of the rotating body 110 via a fixing unit 169a. In addition, the proximal portion of the rotating body 110 is fixed to a distal portion of the elongated member 20 included in the sheath 10.

The elongated member 20 is formed to be rotatable. When the elongated member 20 rotates as shown with an arrow r1 in FIG. 3A, the rotating body 110 rotates as shown with an arrow r2 in FIG. 3A in conjunction along with the rotation of the elongated member 20. In addition, when the rotating body 110 rotates, the breaking member 160 rotates in conjunction along with the rotation of the rotating body 110. In accordance with an exemplary embodiment, since all of the rotating body 110, the elongated member 20, and the breaking member 160 are not fixed (interlocked), the insertion member 130 (the distal member 140 and the proximal member 150) does not rotate in conjunction along with the rotation of each of the members 20, 110, and 160. That is, the insertion member 130 is disposed in a non-rotation state.

Next, shapes of the distal member 140, the proximal member 150, and the breaking member 160 will be described.

Figure 4:
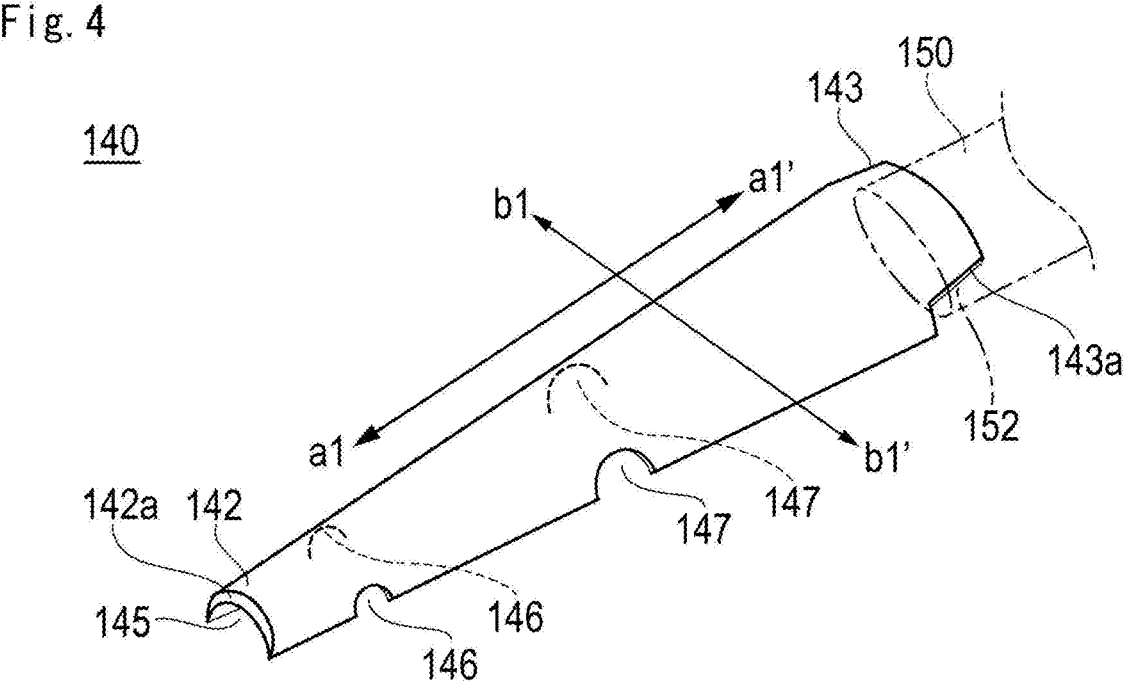
FIG. 4 is a perspective view illustrating a distal portion (distal member) of an insertion member of the medical device according to the embodiment.

FIG. 4 is a perspective view of the distal member 140.

In accordance with an exemplary embodiment, the distal member 140 is formed by a plate-shaped member having a shape curved to one surface side (i.e., a crescent shape, for example, an upper surface side in an illustrated example. In addition, the distal member 140 is formed in a shape that becomes wider from the distal portion 142 side to the proximal portion 143 side (a shape having a dimension in a b1-b1' direction orthogonal to a longitudinal direction a1-a1' shown in FIG. 4, which becomes larger from the distal portion 142 side to the proximal portion 143 side).

Figure 10A:
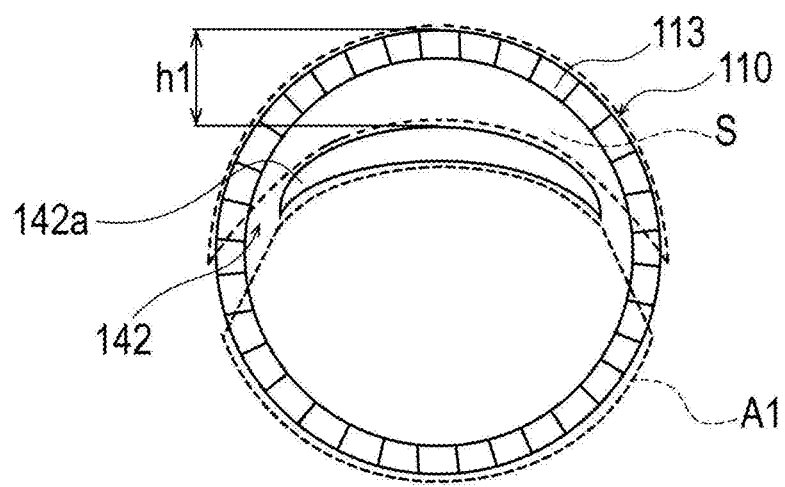
FIG. 10A is a view for describing the action of the medical device according to the embodiment, and is a front view seen from an arrow XA direction shown in FIG. 2A.

As illustrated in FIG. 4 and FIG. 10A (a front view seen from an arrow XA direction shown in FIG. 2A), a distal surface 142a of the distal member 140 can be formed in a shape which is curved in a crescent shape when seen from the front (a shape having a middle portion that has the largest area and an area that gradually decreases from the middle portion to both end portions, when seen from the front). Note that a cross-sectional shape of each portion of the distal member 140 in the longitudinal direction (a cross-sectional shape along a direction orthogonal to the longitudinal direction) can be formed in a shape curved in a crescent shape just as the distal surface 142a (refer to FIG. 10B). In accordance with an exemplary embodiment, the distal member 140 may be formed in a curved shape having a fixed thickness from the middle portion to each of both end portions when seen from the front.

Figure 10B:
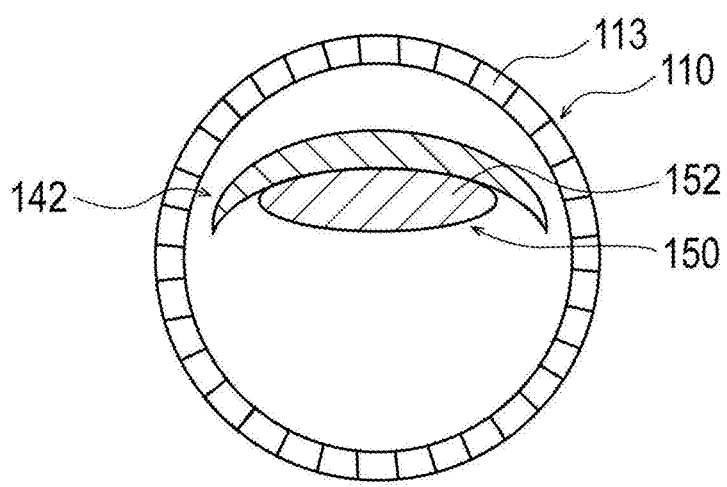
FIG. 10B is a view for describing the action of the medical device according to the embodiment, and is a cross-sectional view along an arrow XB-XB' shown in FIG. 9.

In accordance with an exemplary embodiment, an inner surface of the distal member 140 has a cross-sectional shape which is curved to correspond to an external shape of the distal member 140 (refer to FIG. 10B). In addition, a space portion 145 is formed inside the distal member 140.

In accordance with an exemplary embodiment, a plurality of groove portions 146 and 147 that allow the space portion 145 to communicate with an outside of the space portion 145 are formed in the distal member 140. The groove portions (i.e., distal groove portions) 146 are disposed more distal than the groove portions (i.e., proximal groove portions) 147, and each of groove portions 146 have an area smaller than the groove portions 147. As illustrated, for example, two groove portions 146 are formed to make a pair along a width direction (i.e., the two groove portions 146 being arranged on outer edges of the crescent shaped portion) of the distal member 140. Similarly, for example, two groove portions 147 are formed to make a pair along the width direction of the distal member 140.

In accordance with an exemplary embodiment, the distal portion 152 of the proximal member 150 is inserted inside the proximal portion 143 of the distal member 140 (an inner surface side of the distal member 140). The proximal portion 143 of the distal member 140 and the distal portion 152 of the proximal member 150 are fixed to each other. As a fixing method, it is possible to adopt a known method, for example, bonding, welding, and soldering.

In accordance with an exemplary embodiment, the distal portion 152 of the proximal member 150 has a surface (i.e., side) opposing the proximal portion 143 of the distal member 140. Note that the distal portion 152 of the proximal member 150 may be disposed such that the surface is directly in contact with the distal member 140 as illustrated in FIG. 10B, or for example, a fixing unit (adhesive, a welding portion, and solder) may be disposed between the distal member 140 and a surface opposing the proximal portion 143 of the distal member 140.

A notch portion 143a, which is formed by notching a part of the distal member 140, is formed in the proximal portion 143 of the distal member 140. As illustrated in FIG. 3A, the distal portion 162 of the breaking member 160 is disposed at a position substantially the same as a position where the notch portion 143a is formed (position overlapping in the axial direction). In accordance with an exemplary embodiment, it is possible to provide the notch portion 143a with, for example, an edge surface that exerts a cutting force to the debris D.

Figure 5:
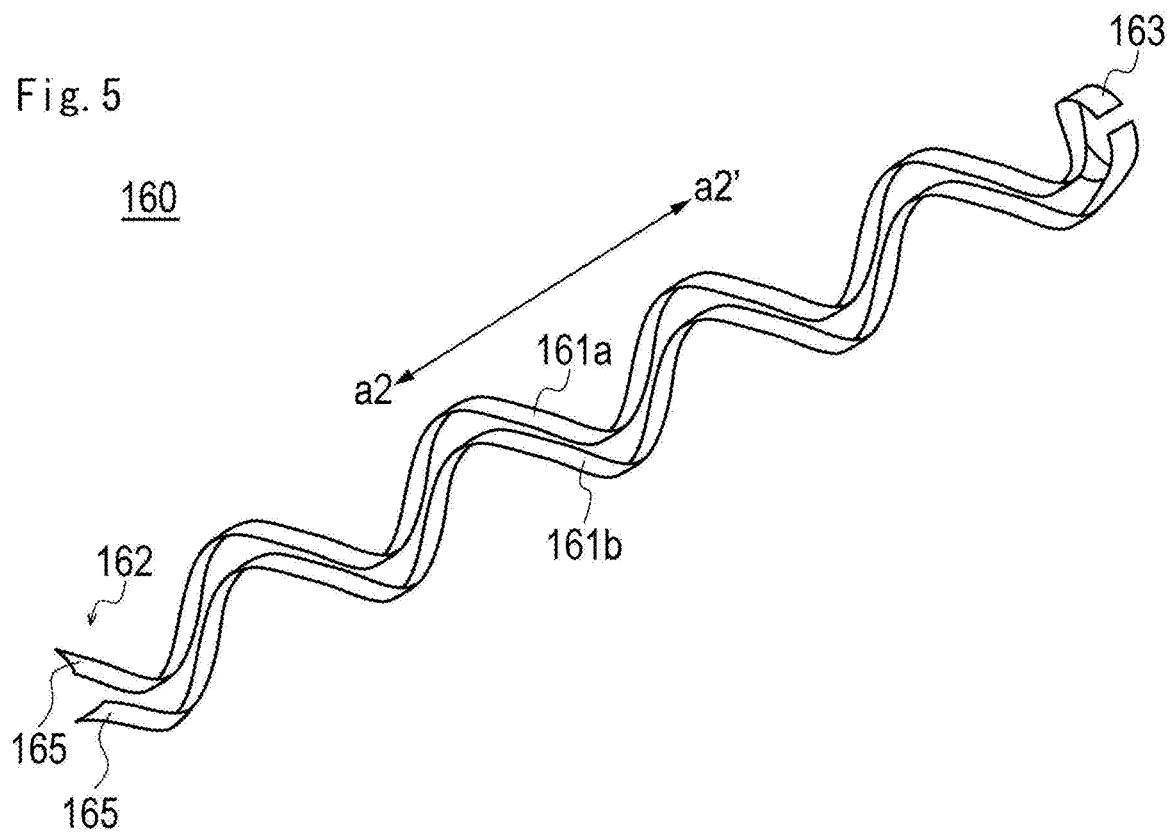
FIG. 5 is a perspective view illustrating a breaking member of the medical device according to the embodiment.

FIG. 5 is a perspective view of the breaking member 160.

The breaking member 160 is formed by a plate-shaped member helically extending in a longitudinal direction (a2-a2' direction).

In accordance with an exemplary embodiment, the breaking member 160 has a first helical portion 161a and a second helical portion 161b that are disposed to oppose each other along the longitudinal direction. The respective helical portions 161a and 161b are in parallel with each other at a predetermined interval, and respectively extend helically (in a wave-like manner). Note that the breaking member 160 is shown as one continuous member in each drawing other than FIG. 4, in order to simplify illustration.

The distal portion 162 of the breaking member 160 (a distal portion of each of the helical portions 161a and 161b) has a relatively sharp shape (edge) forming an edge surface on the distal portion 162. In addition, the proximal portion 163 of the breaking member 160 can include a ring-shaped terminal portion obtained by integrally interlocking the helical portions 161a and 161b with each other.

In accordance with an exemplary embodiment, the distal portion 162 of the breaking member 160 has a shape like a claw having a distal end bent in a predetermined direction (for example, a shape that does not go straight to the distal end and is inclined with respect to the axial direction). Note that the distal portion 162 of the breaking member 160 may be formed, for example, in a shape that extends substantially linearly to go straight in the axial direction.

In accordance with an exemplary embodiment, in a case where the breaking member 160 has a shape that does not go straight to the distal end and is inclined with respect to the axial direction, an intake (transporting capability) into the sheath 10 increases. In addition, in a case where the breaking member 160 has a shape that goes straight to the distal end, break capability with respect to the stenosed site can be improved.

As described above, the distal portion 162 of the breaking member 160 is fixed to the rotating body 110 via the fixing unit 169a (refer to FIG. 3A). The fixing unit 169a can be formed, for example, bonding, welding, and/or soldering. In the embodiment, also in a portion positioned more proximal than the distal portion 162 of the breaking member 160, the breaking member 160 is fixed to the rotating body 110 (refer to a fixing unit 169b in FIG. 3A). Since the breaking member 160 is fixed to the rotating body 110 via the two fixing units 169a and 169b in this manner, the breaking member 160 can be suitably prevented from falling off (i.e., being disengaged from) the rotating body 110. The breaking member 160 may also have a portion that cannot break between an inner surface of the elongated member and the breaking member. In addition, the breaking member 160 may be integrated with the elongated member.

As illustrated in FIG. 3B, the proximal portion 163 of the breaking member 160 is disposed in the vicinity of the proximal portion 153 of the proximal member 150. Note that the proximal portion 163 of the breaking member 160 is disposed along an outer periphery of the proximal portion 153 of the proximal member 150, but the proximal portion is not fixed to the proximal portion 153 of the proximal member 150.

In accordance with an exemplary embodiment, it can be preferable, for example, the breaking member 160 is formed with, for example, a thin plate-shaped member such that the lumen 25 does not become excessively narrow in a state where the breaking member is disposed in the lumen 25 of the sheath 10. In addition, the breaking member 160 can be manufactured, for example, by executing laser processing to a metal tubular member and giving the tubular member a helical shape illustrated in FIG. 5.

Figure 6:
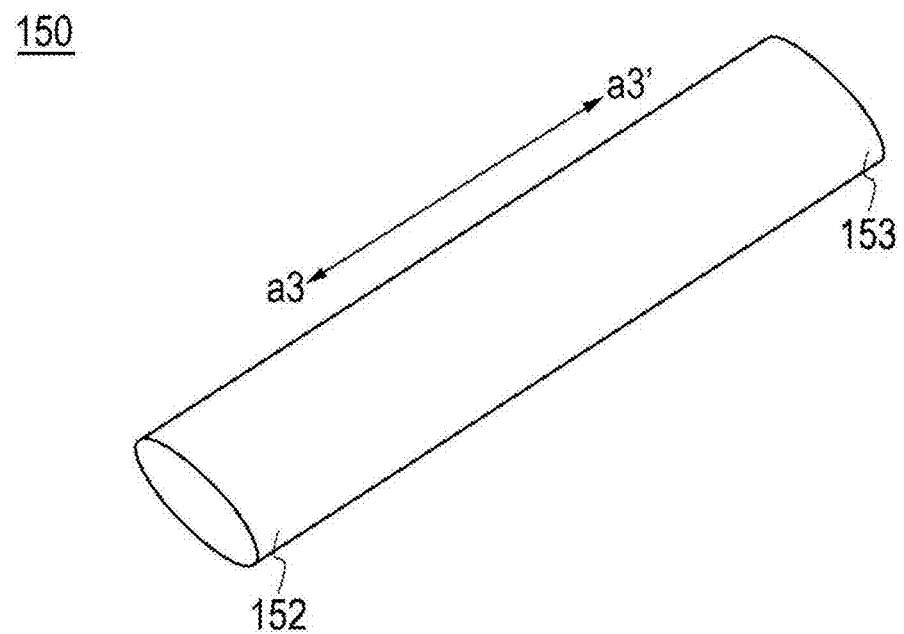
FIG. 6 is a perspective view illustrating a proximal portion (proximal member) of the insertion member of the medical device according to the embodiment.

FIG. 6 is a perspective view of the proximal member 150.

In accordance with an exemplary embodiment, the proximal member 150 is formed by a solid plate-shaped member extending in a longitudinal direction (a3-a3' direction). Note that it is also possible to form the proximal member 150, for example, from a hollow plate-shaped member.

In accordance with an exemplary embodiment, the proximal member 150 is formed such that a cross section along a direction orthogonal to the longitudinal direction is in a substantially fixed shape (i.e., uniform or unchangeable) from the distal portion 152 to the proximal portion 153. In the embodiment, for example, the proximal member 150 has an oblong cross-sectional shape (refer to FIGS. 10B and 10C).

Next, a dispositional relationship between the insertion member 130 (the distal member 140 and the proximal member 150) and the breaking member 160 will be described with reference to FIGS. 3A and 3B.

In accordance with an exemplary embodiment, the breaking member 160 extends from the vicinity of the proximal portion 143 of the distal member 140 to the vicinity of the proximal portion 153 of the proximal member 150. The breaking member 160 is disposed to be helically wound around the distal member 140 and the proximal member 150. In addition, the breaking member 160 is disposed such that each of predetermined gaps g is formed between the distal member 140 and the proximal member 150.

The distal portion 142 of the distal member 140 is disposed to protrude to a side more distal than the distal portion of the rotating body 110. In accordance with an exemplary embodiment, the distal portion 142 of the distal member 140 forms a predetermined guide surface A1 as will be described later (refer to FIGS. 2A and 10A).

A position where the proximal portion 163 of the breaking member 160 is disposed defines a position to which the breaking member 160 transports an object, which is a transporting target, in the end. In the embodiment, in order to make transporting of the object from the rotating body 110 to a position spaced apart to the proximal side by a predetermined distance possible, the position of the proximal portion 163 of the breaking member 160 is set to a predetermined position in the lumen 25 of the sheath 10 as illustrated in FIG. 3B.

Although each dimension related to the insertion member 130 (the distal member 140 and the proximal member 150) and the breaking member 160 is not particularly limited, for example, the following dimension example can be given.

In accordance with an exemplary embodiment, a length (i.e., length in the longitudinal direction) of the distal member 140 can be, for example, 5 mm to 25 mm. In addition, a length by which the distal member 140 protrudes from the rotating body 110 (protrusion length in the axial direction) can be, for example, 3 mm to 20 mm.

In accordance with an exemplary embodiment, a length (i.e., length in the longitudinal direction) of the proximal member 150 can be, for example, 30 to 1,600 mm. In addition, for example, 29.5 mm to 1,599.5 mm of the proximal member 150 can be inserted into the lumen 25 of the elongated member 20.

In accordance with an exemplary embodiment, a length (i.e., length in the longitudinal direction) of the breaking member 160 can be, for example, 28 to 1,598 mm. In addition, for example, 0.3 mm to 10 mm of the breaking member 160 can be inserted into the lumen 115 of the rotating body 110. In addition, for example, approximately 27.7 mm of the breaking member 160 can be inserted into the lumen 25 of the elongated member 20.

Note that although materials configuring the insertion member 130 (the distal member 140 and the proximal member 150) and the breaking member 160 are not particularly limited, it is possible to use, for example, each material exemplified as a material for the rotating body 110.

Next, each configuration member other than the transporting unit 120 (the insertion member 130 and the breaking member 160) included in the distal structure 100 will be described with reference to FIGS. 2A and 2B.

In accordance with an exemplary embodiment, the distal structure 100 has the supporting unit 170 that supports the distal portion 142 of the distal member 140, which protrudes from the rotating body 110, the connection member 175 that fixes (i.e., attaches) the supporting unit 170 to the sheath 10, the guide wire insertion portion 180 that is disposed in a distal portion of the connection member 175, the covering member 190 that integrally connects the supporting unit 170, the guide wire insertion portion 180, and the connection member 175 to each other.

In accordance with an exemplary embodiment, the supporting unit 170 has a first supporting unit 171 and a second supporting unit 172. The first supporting unit 171 is disposed more distal than (i.e., distally of) the second supporting unit 172.

The first supporting unit 171 and the second supporting unit 172 each are formed by a cylindrical member extending in a direction intersecting the axial direction (up-and-down direction shown in FIG. 2B).

In accordance with an exemplary embodiment, the first supporting unit 171 has an outer diameter smaller than an outer diameter of the second supporting unit 172. The distal member 140 is fixed to each of the supporting units 171 and 172. The distal member can be fixed to each of the supporting units 171, 172, for example, by bonding, welding, and/or soldering.

Due to an outer diameter difference between the first supporting unit 171 and the second supporting unit 172, the distal member 140 is disposed in a state where the distal portion 142 side is more inclined to a downward side (downward direction of FIG. 2A) of a height direction than a proximal portion 143 side.

In accordance with an exemplary embodiment, the connection member 175 is fixed to an outer surface of the sheath 10 (i.e., an outer surface of a cover material 30). The connection member 175 can be formed by a rod-like member that extends substantially linearly. The guide wire insertion portion 180 in which a guide wire lumen 185 is formed is fixed to the distal portion of the connection member 175.

In accordance with an exemplary embodiment, the guide wire insertion portion 180 is formed by a hollow member extending in the axial direction. A distal portion of the guide wire insertion portion 180 has a tapered shape, which tapers towards the distal side, in order to make smooth movement in a body lumen, such as the blood vessel H, possible. Note that a shape, a length, an outer diameter, an inner diameter, and a material for the guide wire insertion portion 180 are not particularly limited. In accordance with an exemplary embodiment, it can be possible to achieve making the diameter of the distal structure 100 smaller, for example, by disposing the guide wire insertion portion 180 to extend substantially linearly along the axial direction as illustrated.

Accordingly, the insertability (deliverability) of the medical device 1 with respect to the stenosed site S can be relatively improved.

In accordance with an exemplary embodiment, the covering member 190 connects the members 140, 175, and 180 to each other in a state of covering a proximal portion of the guide wire insertion portion 180, the distal portion of the connection member 175, and the distal portion 142 of the distal member 140. The covering member 190 can be formed by, for example, a known heat-shrink tube. As the heat-shrink tube, it is possible to use a hollow member made from, for example, fluorine-based resins such as an ethylene tetrafluoroethylene (ETFE) copolymer and polytetrafluoroethylene (PTFE), polyolefins such as polyethylene (PE) and polypropylene (PP), polyamides, polyesters, and polyurethane.

Note that a method of connecting the guide wire insertion portion 180, the connection member 175, and the distal member 140 to each other is not limited to the method in which the covering member 190 is used, and it is also possible to adopt, for example, bonding, welding, soldering, and/or by means of a fixing member such as adhesive tape.

Materials configuring the supporting unit 170, the connection member 175, and the guide wire insertion portion 180 are not particularly limited, and it is possible to use, for example, a known resin material or a known metal material.

Next, the guide surface A1 formed by the distal member 140 and the supporting unit 170 will be described.

As illustrated in FIG. 2A, the guide surface A1 is formed on the distal side of the rotating body 110 by the distal member 140 and the supporting unit 170. In addition, as illustrated in FIG. 10A, the distal member 140 and the supporting unit 170 cover (shield) a part of a distal surface of the rotating body 110 (an end surface of the cutting unit 113) when the distal structure 100 is seen from the front. A range where the cutting unit 113 of the rotating body 110 can come into contact with the stenosed site S is limited to a range h1 where the guide surface A1 is not formed (hereinafter, referred to as an effective cutting range).

As described above, advantages of setting the effective cutting range h1 will be described with reference to FIGS. 8 and 10A. FIGS. 8 and 10A schematically illustrate a state when cutting the stenosed site S formed in the blood vessel H by using the medical device 1.

When cutting the stenosed site S, a practitioner rotates the rotating body 110 as shown in the arrow r2 in FIG. 8. In addition, the practitioner brings the cutting unit 113 closer to the stenosed site S in a state where the rotating body 110 is rotated, and cuts the stenosed site S. For example, when the rotating body 110 unintentionally goes beyond the stenosed site S and reaches a blood vessel wall positioned on an upper side in FIG. 8 in the middle of performing such a procedure, a risk of the cutting unit 113 penetrating (piercing) the blood vessel wall can occur. On the contrary, when a range where the cutting unit 113 exerts a cutting force is limited to the effective cutting range h1 by the guide surface A1 as described above, a risk of the cutting unit 113 penetrating the blood vessel wall significantly decreases. Note that it becomes possible to reliably prevent the penetration of the blood vessel wall by setting the effective cutting range h1 to be smaller than a thickness of the blood vessel wall.

In a case of improving the efficiency of cutting by the cutting unit 113, the size of the effective cutting range can be adjusted, for example, by changing the shape of the rotating body 110 and the outer diameter of the cutting unit 113, after considering a balance between the efficiency of cutting and a risk of penetrating the blood vessel wall. By performing such adjustment, it becomes possible to achieve both of the relative efficiency of cutting and improvement in safety.

Next, the sheath 10 will be described.

Figure 7A:
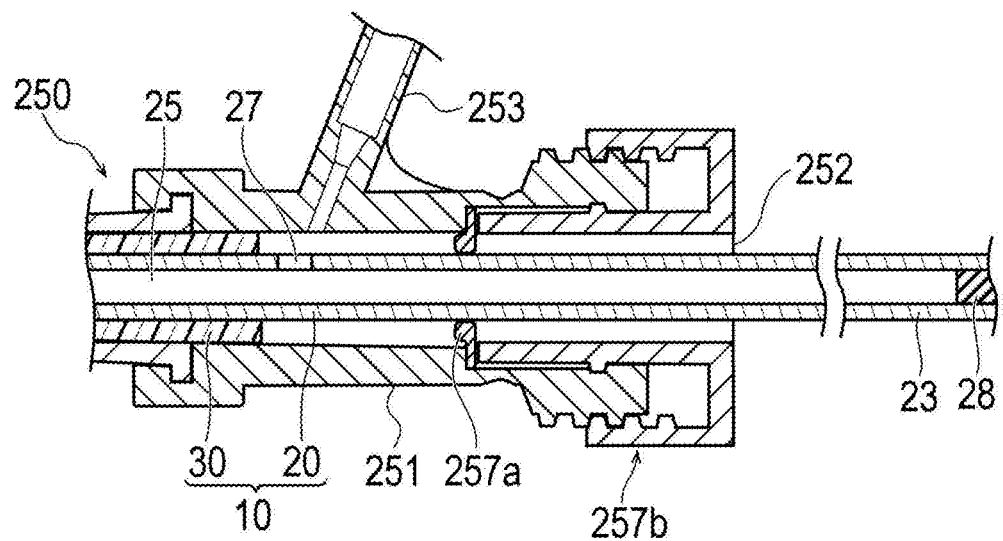
FIG. 7A is an enlarged cross-sectional view of a hand operation unit of the medical device according to the embodiment.
Figure 7B:
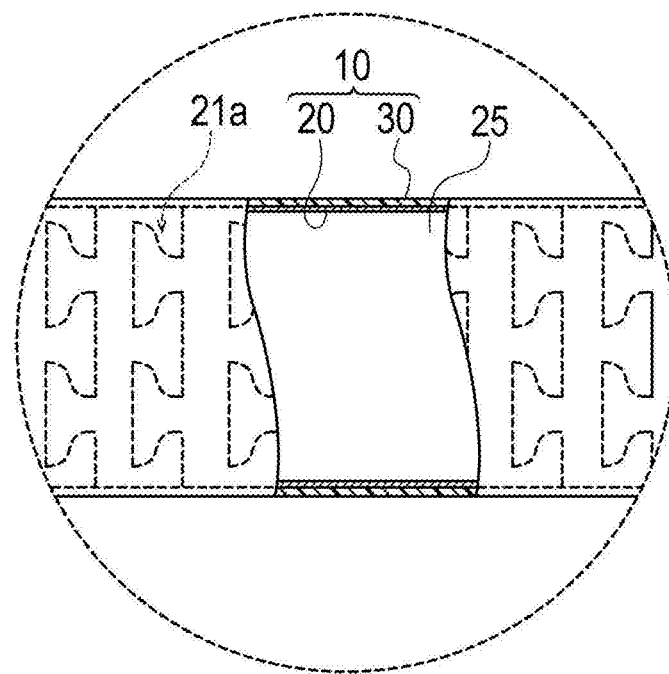
FIG. 7B is an enlarged cross-sectional view of an elongated member and a cover material according to the embodiment.

As illustrated in FIG. 7B (a partially enlarged cross-sectional view of the sheath 10), the sheath 10 has the elongated member 20 and the cover material (outer layer) 30.

The elongated member 20 is formed by a metal tubular member that has the lumen 25 extending in the axial direction. In accordance with an exemplary embodiment, a predetermined slit 21a can be formed in the elongated member 20. By the slit 21a being formed, the elongated member 20 becomes a member having improved curvature in a body lumen such as the blood vessel H. Note that a specific shape of the slit 21a is not particularly limited. In addition, it is also possible to form, for example, a plurality of patterns of slits having different sizes or shapes in the elongated member 20.

In accordance with an exemplary embodiment, the cover material 30 is disposed to cover an outer surface of the elongated member 20. The cover material 30 helps protect biological tissues in a living body from the elongated member 20. In addition, the cover material 30 helps prevent an object (the debris D or a floating thrombus) in the lumen 25 of the elongated member 20 from flowing out to the outside of the elongated member 20. As to the cover material 30, it is possible to use a hollow member (tubular member) made from a known resin material, for example, polyethylene, polypropylene, and a polyamide.

Note that a structure or a material for the elongated member 20 is not particularly limited as long as the material of the elongated member 20 can transmit a rotational drive force from the proximal side to the distal side of the elongated member 20 (from a hand operation unit 250 side to a rotating body 110 side). For example, the elongated member 20 can be made from a resin tube formed by a single layer or a plurality of layers, a resin tube to which a reinforcement member such as a blade is added, a metal pipe to which spiral processing is executed, and a hollow coil spring that can expand and contract in the axial direction.

In accordance with an exemplary embodiment, the elongated member 20 is fixed (i.e., attached) to the rotating body 110. In the embodiment, as illustrated in FIG. 3A, each of the members 10 and 110 is fixed in a state where a proximal surface of the rotating body 110 and a distal surface of the elongated member 20 are aligned such that a seam between an inner surface of the rotating body 110 and the inner surface of the elongated member 20 is flat (smooth). In accordance with an exemplary embodiment, it is possible to adopt a method, for example, bonding, fusion, and welding as a fixing method of the elongated member 20 and the rotating body 110 after considering a material for each of the members 10 and 110.

Although each dimension of the sheath 10 (the elongated member 20 and the cover material 30) is not particularly limited, an inner diameter of the elongated member 20 can be, for example, 0.7 mm to 2.5 mm, an outer diameter of the elongated member 20 can be, for example, 0.8 mm to 2.6 mm, and a length along the axial direction of the elongated member 20 can be, for example, 300 mm to 1,600 mm. In addition, an inner diameter of the cover material 30 can be, for example, 0.9 mm to 2.7 mm, an outer diameter of the cover material 30 can be, for example, 1.0 mm to 3.0 mm, and a length of the cover material 30 along the axial direction can be, for example, 300 mm to 1,600 mm.

Next, the hand operation unit 250 will be described.

In accordance with an exemplary embodiment, as illustrated in FIG. 1, the hand operation unit 250 has a hub 251, a connector unit 253 provided in the hub 251, and a port 255 provided in the connector unit 253.

A proximal portion 23 of the elongated member 20 can be inserted into the hub 251 to be guided out from a proximal port 252 of the hub 251. A valve body 257a that helps prevent leakage of a fluid from the proximal port 252 is disposed in a proximal portion of the hub 251.

A proximal portion 33 of the cover material 30 that covers the elongated member 20 is inserted in the hub 251, and is fixed at a predetermined position in the hub 251. Note that the cover material 30 is not fixed (interlocked) to the elongated member 20 and the rotating body 110.

In the port provided in the connector unit 253, a flow path through which a fluid can flow is formed. The connector unit 253 can be configured, for example, by a Luer taper connector, which is known in the medical field.

In accordance with an exemplary embodiment, a three-way stopcock for operating the flow of a fluid can be disposed in the port 255. The port 255 can be interlocked with an aspiration device 290, for example, via a tube 291 through which the fluid can flow. The aspiration device 290 can be formed, for example, by a known fluid aspiration pump that can generate negative pressure.

The proximal portion of the elongated member 20 is configured to be capable of being connected to an external drive apparatus 280 via a predetermined connector (not illustrated). In accordance with an exemplary embodiment, a drive source that is configured by a known electric motor generating a drive force for rotating the elongated member 20 is included in the external drive apparatus 280.

When the external drive apparatus 280 is operated to exert a rotational force to the elongated member 20, the elongated member 20 rotates as shown with the arrow r1 in FIG. 3A. When the elongated member 20 rotates, the rotating body 110 fixed to the distal portion of the elongated member 20 and the breaking member 160 fixed to the rotating body 110 rotate as shown with the arrow r2 in FIG. 3A. Note that the cover material 30 does not rotate even in a case where the elongated member 20 rotates since the cover material is not fixed to the elongated member 20 and the rotating body 110.

In accordance with an exemplary embodiment, it is possible, for example, for a control unit (not illustrated) to perform operation control of the external drive apparatus 280 and the aspiration device 290. In accordance with an exemplary embodiment, the control unit can be, for example, a known microcomputer, including a CPU, a RAM, and a ROM. In addition, for example, the control unit may be mounted on the external drive apparatus 280 or the aspiration device 290, or may be incorporated in another device other than the external drive apparatus 280 and the aspiration device 290 and perform transmission and reception of a control signal between each of the devices 280 and 290 and the control unit in a wired or wireless manner. In addition, the control unit can include electric circuits including a battery and switches and can also include a microcomputer, including a CPU, a RAM, and a ROM.

In accordance with an exemplary embodiment, during various procedures, the rotating body 110 may be rotated in either a clockwise direction or a counterclockwise direction. In addition, the clockwise direction and the counterclockwise direction may be switched and the rotating body may be rotated as appropriate.

As illustrated in FIG. 7A, the elongated member 20 has an opening portion 27 disposed in the vicinity of the connector unit 253 of the hand operation unit 250. The lumen 25 of the elongated member 20 communicates with the inside of the connector unit 253 of the hand operation unit 250 via the opening portion 27.

In order to help prevent an aspiration force from being applied to a side more proximal than the proximal portion 23 of the elongated member 20 via the opening portion 27, a predetermined obstructive member 28 that blocks the lumen 25 can be disposed in the vicinity of the proximal portion 23 of the elongated member 20. The obstructive member 28 can be formed by, for example, an elastic member.

In accordance with an exemplary embodiment, the valve body 257a can be disposed inside the hand operation unit 250 and configured to be switched between an open state and a closed state by operating an opener (plunger) 257b provided in the hand operation unit 250. In accordance with an exemplary embodiment, a valve body and an opener that have the same structures as those used in a known Y-connector can be used as the valve body 257a and the opener 257b.

Next, an example of procedures of a technique in which the medical device 1 is used will be described with reference to FIGS. 8 to 10C.

Figure 9:
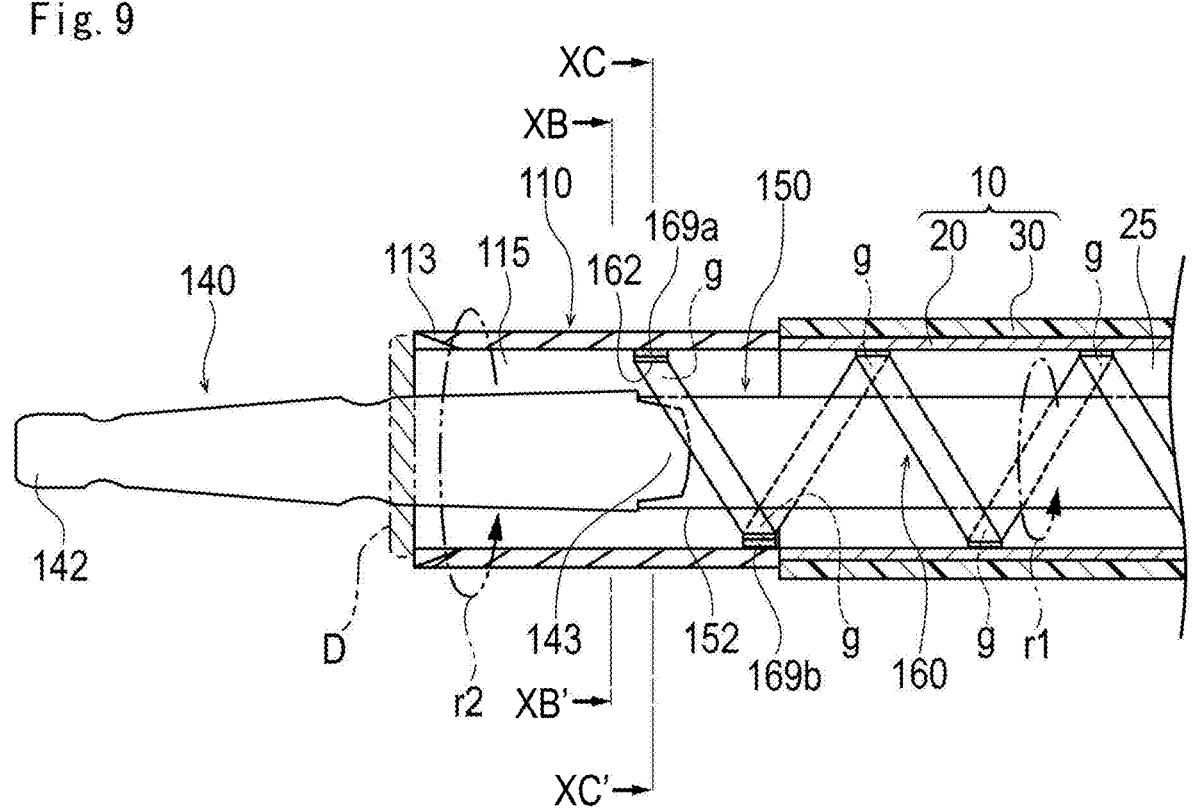
FIG. 9 is a view for describing action of the medical device according to the embodiment, and is a cross-sectional view corresponding to FIG. 3A.
Figure 10C:
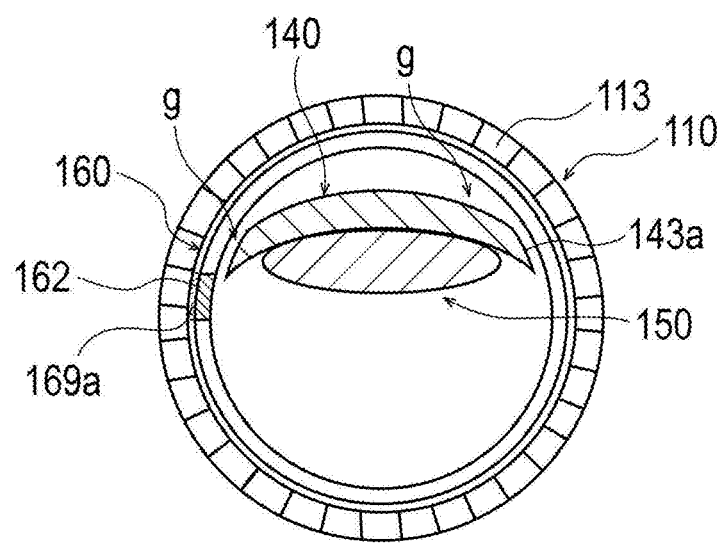
FIG. 10C is a view for describing the action of the medical device according to the embodiment, and is a cross-sectional view along an arrow XC-XC' shown in FIG. 9.

FIG. 8 schematically illustrates a state when the cutting of the stenosed site S formed in a blood vessel H is performed by using the medical device 1, and FIG. 9 illustrates a state when transporting the debris D generated in the middle of performing the procedure shown in FIG. 8 to the proximal side of the lumen 25 of the sheath 10. In addition, FIG. 10A is a front view seen from the arrow XA direction shown in FIG. 2A, FIG. 10B is a cross-sectional view along an arrow XB-XB' line illustrated in FIG. 9 (axially orthogonal cross-sectional view), and FIG. 10C is a cross-sectional view along an arrow XC-XC' line illustrated in FIG. 9 (axially orthogonal cross-sectional view).

First, a practitioner (i.e., operator) introduces a guiding sheath (not illustrated) to the vicinity of the stenosed site S. The guiding sheath can be delivered to the vicinity of the stenosed site S along a guide wire (not illustrated) introduced prior to the introduction of the guiding sheath. Note that it is also possible to omit the use of the guide wire as appropriate when delivering the guiding sheath.

Next, the practitioner delivers the medical device 1 to the vicinity of the stenosed site S via the guiding sheath. At this time, a guide wire w is inserted into the guide wire insertion portion 180. The practitioner can smoothly deliver the medical device 1 to the vicinity of the stenosed site S by directing the medical device along the guide wire w to the stenosed site S.

Next, the practitioner pushes the cutting unit 113 of the rotating body 110 to the stenosed site S while rotating the rotating body 110 as shown with the arrow r2. The cutting unit 113 scrapes a stenosis object (for example, plaque or a thrombus) included in the stenosed site S by exerting a cutting force to the stenosed site S.

As illustrated in FIG. 10A, since the guide surface A1 is formed on the distal side of the rotating body 110, a range where the cutting unit 113 of the rotating body 110 can come into contact with the blood vessel wall is limited to the effective cutting range h1. Accordingly, it is possible to significantly decrease a risk of the cutting unit 113 penetrating the blood vessel wall.

In the embodiment, the distal member 140 is formed by a plate-shaped member (a member having a shape that spreads in a right-and-left direction on the cross section illustrated in FIG. 10A). For this reason, as illustrated in FIG. 10A, the guide surface A1 having a relatively large area can be formed. Since the distal member 140 has a cross-sectional shape that spreads in the width direction, the distal member 140 is supported by staying in contact with an inner peripheral surface of the rotating body 110, for example, even when the position of the distal member 140, for example, is carelessly shifted in an up-and-down direction shown in FIG. 10A in the middle of performing a procedure to the stenosed site S. Therefore, a shift in the position of the distal member 140 can be suitably suppressed.

As illustrated in FIG. 10A, the distal member 140 is formed in a shape, of which a cross-sectional shape along a direction orthogonal to the axial direction is curved in a crescent shape. For this reason, the stenosed site S is scraped into a crescent shape (peel shape) having a relatively small thickness.

When cutting the stenosed site S with the cutting unit 113, for example, the practitioner operates the aspiration device 290 illustrated in FIG. 1 to aspirate the scraped debris D into the lumen 115 of the rotating body 110. When operating the aspiration device 290 while rotating the rotating body 110, an aspiration force pulling the debris D increases due to convection induced along with the rotation of the rotating body 110. Therefore, the debris D smoothly moves to the lumen 115 of the rotating body 110.

In accordance with an exemplary embodiment, the debris D aspirated in the lumen 115 of the rotating body 110 can be sandwiched (i.e., located) between the distal portion 162 of the breaking member 160 and the proximal portion 143 of the distal member 140. Then, when the breaking member 160 rotates relative to the distal member 140 along with the rotation of the rotating body 110, a shearing force is exerted to the debris D sandwiched between the distal portion 162 of the breaking member 160 and the proximal portion 143 of the distal member 140, and thus the debris D is finely broken (severed).

In addition, an object to be cut that enters the lumen 115 of the rotating body 110 is generated in some cases in a state where a part of the object is still connected to the stenosed site S without being completely separated away from the stenosed site S. As the object to be cut being sandwiched between the distal portion 162 of the breaking member 160 and the proximal portion 143 of the distal member 140, the medical device 1 exerts tension (a force of stretching in the axial direction) to the object to be cut. Then, the cutting unit 113 of the rotating body 110 exerts a cutting force to the part of the object to be cut, which is connected to the stenosed site S, in a state where the tension is exerted to the object to be cut, and cut out the object to be cut from the stenosed site S. By performing cutting by the cutting unit 113 of the rotating body 110 in a state where the tension is exerted to the object to be cut, it becomes possible for the medical device 1 to rather easily separate the object to be cut.

In addition, since the distal portion 162 of the breaking member 160 is formed in a sharp shape (refer to FIG. 5) in the embodiment, the debris can be finely severed by the distal portion 162 of the breaking member 160 when the debris D aspirated in the lumen 115 of the rotating body 110 reaches the vicinity of the proximal portion 143 of the distal member 140 (the vicinity of a place where the distal portion 162 of the breaking member 160 is disposed).

The debris D aspirated in the lumen 115 of the rotating body 110 is sandwiched in the gaps g formed between the breaking member 160 and the distal member 140.

When the breaking member 160 rotates along with the rotation of the rotating body 110, shearing stress is applied to the debris D between the distal member 140 and the breaking member, thereby breaking the debris D. In addition, when the breaking member 160 rotates, the debris D is transported to the proximal side due to a rotational force applied between the breaking member 160 and the distal member 140.

In a state of being sandwiched in the gaps g between the distal member 140 and the breaking member 160 and the gaps g between the proximal member 150 and the breaking member 160, the debris D is transported to the proximal side of the lumen 25 via each of the gaps g while being shorn with the rotation of the breaking member 160. Then, in accordance with an exemplary embodiment, the debris D can be broken to a size that will not cause clogging of the lumen 25 until the debris D reaches the proximal portion 163 of the breaking member 160 (refer to FIG. 3B). For this reason, the debris D can be prevented from clogging the lumen 25, and it is possible to smoothly transport the debris D to a proximal portion side of the sheath 10 (the hand operation unit 250 side).

In accordance with an exemplary embodiment, the practitioner continues operation of pushing the cutting unit 113 of the rotating body 110 to the stenosed site S, and moves the medical device 1 to the distal side (the left in FIG. 8). By performing this operation, the stenosed site S can be cut along a direction where the stenosed site S extends. After checking that a cutting procedure with respect to the stenosed site S is completed, the practitioner withdraws the medical device 1 from a living body as appropriate. Note that it is also possible to subsequently execute a procedure with respect to another stenosed site S.

As described above, a method of the procedure according to the embodiment includes exerting a shearing force to a predetermined object to break (sever) the object by rotating the breaking member 160 relative to the insertion member 130 in a state where a part of the predetermined object (the stenosed site S or the debris D severed from the stenosed site S) is sandwiched in the gaps g formed between the insertion member 130 inserted in the lumen 25 of the elongated member 20 and the distal portion 162 of the breaking member 160 disposed on the inner surface of the elongated member 20.

In accordance with an exemplary embodiment, the method of the procedure includes separating out a part of the stenosed site S by exerting tension to the part of the stenosed site S with the part of the stenosed site S sandwiched in the gaps g and exerting a cutting force to the stenosed site S via the cutting unit 113 of the rotating body 110, which is disposed on the distal portion of the elongated member 20.

In accordance with an exemplary embodiment, the method of the procedure includes exerting a shearing force in a state where the part of the stenosed site S is hooked with a claw-like portion formed in the distal portion 162 of the breaking member 160.

In accordance with an exemplary embodiment, the method of the procedure includes exerting a cutting force to the part of the stenosed site S with a sharp portion formed in the distal portion 162 of the breaking member 160.

In accordance with an exemplary embodiment, the method of the procedure includes transporting the object, which is broken (severed) in a state of being sandwiched in the gaps g, to the proximal side of the elongated member 20 via the plurality of gaps g formed between the insertion member 130 and the breaking member 160.

In accordance with an additional exemplary embodiment, the method of the procedure includes a step of transporting the debris D stored inside the sheath 10 to a distal direction to discharge to the distal side of the rotating body 110 by driving the rotation of the rotating body 110 in a rotation direction opposite to a direction when cutting the stenosed site S, after the practitioner taking the medical device 1 out from a living body. By executing such a step, the practitioner can rather easily check a state (size or properties) of the debris D.

Next, the action of the medical device 1 according to the embodiment will be described.

As described above, the medical device 1 has the elongated member 20 in which the lumen 25 extending in the axial direction is formed, the insertion member 130 of which at least a part is inserted in the lumen 25 of the elongated member 20 on the distal side, and the breaking member 160 that is disposed around the insertion member 130 to form the gaps g between the insertion member 130 and the breaking member in the lumen 25 of the elongated member 20 on the distal side and transports an object (the debris D or a floating thrombus), which is a transporting target, to the proximal side of the lumen 25 along with relative rotation to the insertion member 130.

With the object, which is the transporting target, sandwiched in the gaps g formed between the breaking member 160 and the insertion member 130, the medical device 1 can exert a shearing force to the object when the breaking member 160 rotates relative to the insertion member 130. For this reason, the medical device 1 can help prevent the object, which is the transporting target, from clogging the lumen 25 of the elongated member 20.

In addition, when an object, which is a transporting target, is sandwiched between a distal portion 162 of the breaking member 160 and the proximal portion 143 of the distal member 140, for example, as shown in FIGS. 3B and 5, the object can be firmly sandwiched between the distal portion 162 of the breaking member 160 and the proximal portion 143 of the distal member 140 since the distal portion 165 of the breaking member 160 has a shape bent in a predetermined direction. Therefore, a shearing force can be efficiently exerted to the object.

In addition, the elongated member 20 can be configured to be rotatable, and the rotating body 110 that rotates along with the rotation of the elongated member 20 is disposed on the distal portion of the elongated member 20. The insertion member 130 is disposed in a non-rotation state such that the insertion member does not rotate in conjunction along with the rotation of the elongated member 20. The breaking member 160 is fixed (i.e., attached) to the rotating body 110, and rotates along with the rotation of the elongated member 20. Since the medical device 1 is configured as described above, the breaking member 160 can be smoothly rotated in conjunction along with the rotation of the elongated member 20 and the rotating body 110. Accordingly, an object, which is a transporting target, can be rather easily moved to the proximal side of the lumen 25.

In addition, the rotating body 110 has the cutting unit 113 that applies a cutting force with the rotation. For this reason, the medical device 1 can be used as a device for performing cutting of the stenosed site S.

In addition, the rotating body 110 has a hollow shape into which the insertion member 130 can be inserted. The distal portion of the insertion member 130 (the distal portion 142 of the distal member 140) protrudes to a side more distal than the distal portion of the rotating body 110, and is disposed at a position of overlapping a part of the cutting unit 113 and exposing a part of the cutting unit 113 when seen from the distal side of the rotating body 110. For this reason, when cutting the stenosed site S, the medical device 1 can limit a range where the cutting unit 113 can cut by means of the guide surface A1 disposed on the distal side of the rotating body 110. Accordingly, even when the rotating body 110 reaches a blood vessel wall of the blood vessel H in the middle of a procedure, the medical device 1 can prevent the rotating body 110 from penetrating the blood vessel wall.

In addition, the distal portion of the insertion member 130 (the distal portion 142 of the distal member 140) is formed by a plate-shaped member. For this reason, since it is possible to form the guide surface A1, which is formed on the distal side of the rotating body 110, to have a relatively large size, a range where the cutting unit 113 can cut can be adjusted to have an appropriate size.

In addition, the distal portion of the insertion member 130 (the distal member 140) is formed in a shape, of which a cross-sectional shape along the direction orthogonal to the axial direction is curved in a crescent shape. For this reason, the cutting unit 113 of the rotating body 110 can scrape the stenosed site S into a crescent shape having a relatively small thickness. Consequently, the debris D can be prevented from clogging the lumen 25 of the elongated member 20.

In addition, the distal portion 162 of the breaking member 160 can be formed in a sharp shape. For this reason, since it is possible for the distal portion 162 of the breaking member 160 to cut the debris D, the debris D can be prevented from clogging the lumen 25 of the elongated member 20.

In addition, since the breaking member 160 is formed by a plate-shaped member, which extends helically, the breaking member can rather easily move the debris D which is sandwiched in the gaps g formed between the breaking member 160 and the insertion member 130 to the proximal side in conjunction along with the rotation of the breaking member 160. It is possible to efficiently exert a shearing force to the debris D between the breaking member 160 and the insertion member 130. Since the breaking member 160 is plate-shaped, a space in the lumen 25 can be prevented from becoming excessively narrow due to the disposition of the breaking member 160.

In addition, the breaking member 160 extends over a predetermined range (i.e., at least a length that the breaking member 160 opposes a proximal end portion 143 of the distal member 140) from the distal side of the lumen 25 to the proximal side of the lumen 25 of the elongated member 20. For this reason, the debris D can be reliably transported to a predetermined position of the lumen 25 on the proximal side in conjunction along with the rotation of the breaking member 160.

Hereinafter, a modification example of the embodiment described above will be described.

Modification Example

Figure 11:
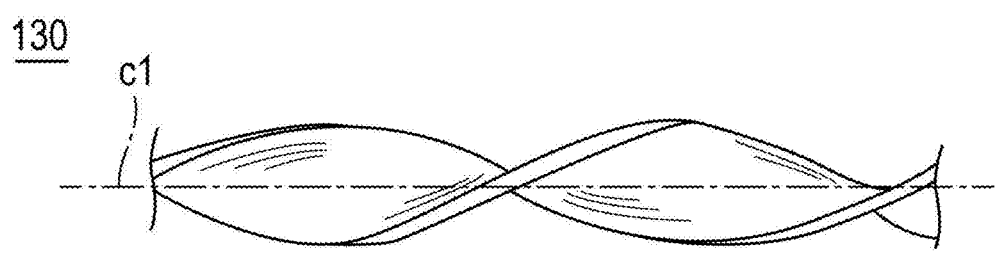
FIG. 11 is a view illustrating an insertion member according to a modification example.

For example, as illustrated in FIG. 11, the insertion member 130 can be formed in a shape of which a cross-sectional shape along a direction orthogonal to the axial direction of the sheath 10 (a direction along an axis c1 illustrated in FIG. 11) is not a perfect circle. For example, the insertion member 130 can be formed in a shape twisted with respect to the axial direction as illustrated in FIG. 11. With the insertion member 130 formed in this manner, shearing stress is likely to occur, and severing becomes rather easy.

Figure 12:
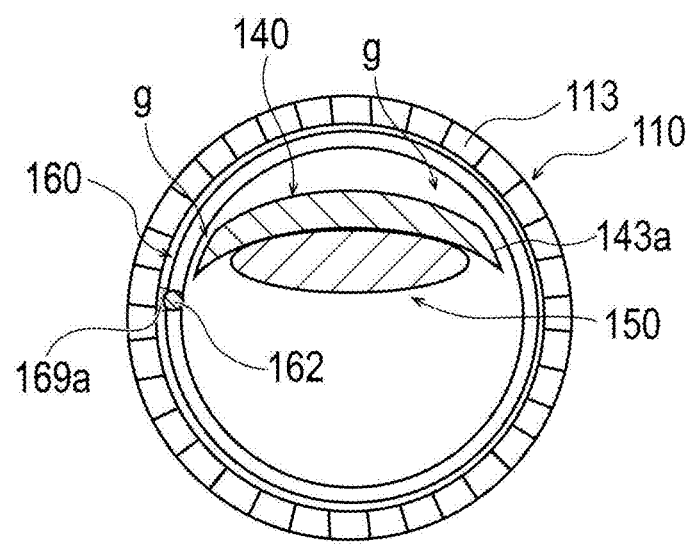
FIG. 12 is a view illustrating a breaking member according to the modification example.

In addition, for example, as illustrated in FIG. 12, the distal portion 162 of the breaking member 160 can be formed to have a perfect circle cross-sectional shape. With the breaking member 160 formed in this manner, a severing effect caused by stretching can be added in addition to shearing stress.

Figure 13:
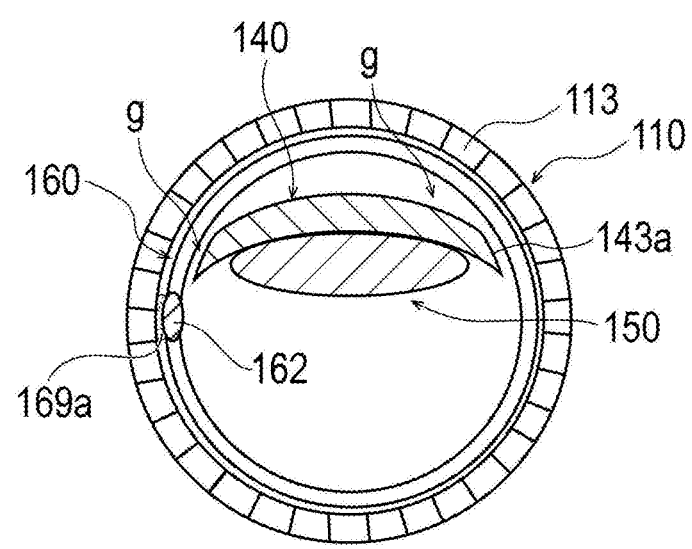
FIG. 13 is a view illustrating the breaking member according to the modification example.

In addition, for example, as illustrated in FIG. 13, the distal portion 162 of the breaking member 160 can be formed to have a non-circular cross-sectional shape. For example, the distal portion 162 of the breaking member 160 can be formed to have an oblong cross-sectional shape. With the breaking member 160 formed in this manner, shearing stress is likely to occur, and severing becomes rather easy.

Figure 14:
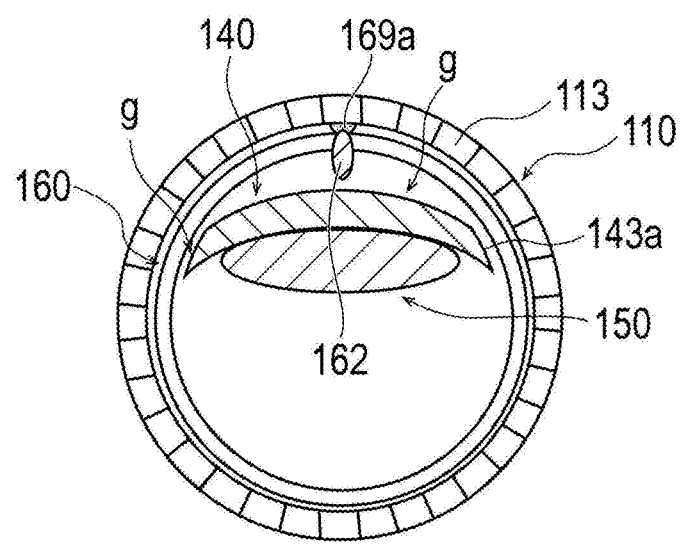
FIG. 14 is a view illustrating the breaking member according to the modification example.

In addition, for example, as illustrated in FIG. 14, the distal portion 162 of the breaking member 160 is disposed to have a convex shape toward a center side of a rotation direction of the breaking member 160 rather than a circumferential direction side along the rotation direction. In a case where the distal portion 162 of the breaking member 160 is formed to have an oblong cross-sectional shape as illustrated in FIG. 14, the distal portion can be disposed such that a central axis along a major axis direction of the ellipse faces a center side of the rotating body 110. With the breaking member 160 formed in this manner, shearing stress is likely to occur, and severing becomes rather easy.

In addition, in a case where the breaking member 160 is formed with a plate-shaped member and the insertion member 130 is formed with a plate-shaped member, an object (the debris D) can be prevented from clogging the lumen 25 of the elongated member 20 since a volume of the lumen 25 of the elongated member 20 (volume excluding the insertion member 130) can be secured to be relatively large. Since shearing stress is likely to occur due to the breaking member 160 formed in a plate shape and the insertion member 130 formed in a plate shape, it can be rather easy to sever the object.

In addition, in a case where one of the breaking member 160 and the insertion member 130 is formed with a plate-shaped member and the other is a member having a circle cross-sectional shape that is not a perfect circle, an object can be prevented from clogging the lumen 25 of the elongated member 20 since the volume of the lumen 25 of the elongated member 20 (volume excluding the insertion member 130) can be secured to be relatively large. In a case where one of the breaking member 160 and the insertion member 130 is a plate-shaped member and the other is a member having a circle cross-sectional shape that is not a perfect circle, a severing effect caused by stretching of an object, which is a severing target, can be added in addition to shearing stress. In addition, in a case where both of the breaking member 160 and the insertion member 130 are formed by a member having a cross-sectional shape that is not a perfect circle, a severing effect caused by stretching of an object, which is a severing target, can be added in addition to shearing stress.

Although the medical device according to the present disclosure is described through the embodiment hereinbefore, the present disclosure is not limited to only the content described in the embodiment, and can be changed as appropriate based on the scope of claims.

For example, a body lumen, which is a target of various types of procedures performed by using the medical device, is not limited to the blood vessel, and may be, for example, a vessel, a ureter, a bile duct, a fallopian tube, and a hepatic duct.

For example, it is also possible to configure the medical device as a device that does not have a rotating body exerting a cutting force to a stenosed site. In addition, even in a case where the rotating body is added to the medical device, an object, which is a cutting target, is not limited to the stenosed site or an obstructive part. Note that although an example in which a procedure of cutting a stenosed site formed in a part of a wall portion of a body lumen in a circumferential direction is given in the description of the embodiment, the use or a function of the medical device is not limited by a shape of the stenosed site or a circumferential position to be formed.

Although a configuration where a shearing force is exerted to an object by rotating the breaking member with respect to the insertion member is shown in the description of the embodiment, the exertion of a shearing force to the object may be realized by relative rotation between the insertion member and the breaking member. Therefore, it is also possible to configure the medical device such that a shearing force is exerted to an object by the insertion member rotating with respect to the breaking member. Note that although an example in which the breaking member is fixed to the rotating body in order to make the breaking member rotatable is given in the embodiment, for example, the breaking member may be fixed to the elongated member, or may be fixed to both of the elongated member and the rotating body.

Although an example in which the insertion member is formed by two members including the distal member and the proximal member is given in the description of the embodiment, the insertion member may be formed by one member, or may be formed by three or more members.

In addition, for example, a specific shape of the insertion member is not limited to the shape described with illustration. For example, it is also possible to configure the insertion member with a flat plate-shaped member having a rectangular cross section, to configure the insertion member with a plate-shaped member having cross-sectional shapes which differ according to each portion in the axial direction, or to configure the insertion member with a round rod-like member. In addition, even in a case where the insertion member is configured such that a cross-sectional shape of insertion member is a curved shape, the cross-sectional shape may be a shape other than a crescent shape, or it is possible to change also the curvature of the curved shape as appropriate. Similarly, also a shape of the proximal member is not limited to the illustrated shape, and it is also possible to configure the proximal member, for example, with a hollow (cylindrical) member.

Although an example in which two cylindrical members are used as members configuring the supporting unit is described in the embodiment, for example, the supporting unit may be formed by only one member, or may be formed by three or more members. In addition, also a specific shape or a size of a member configuring the supporting unit is not particularly limited.

Although an example in which a plate-shaped member extending helically is used as the breaking member is given in the embodiment, the breaking member is not limited to a specific shape insofar as it is possible to transport an object to the proximal side along with relative rotation with respect to the insertion member.

Although an example of a configuration where the breaking member extends over a fixed range of the lumen of the elongated member is given in the description of the embodiment, the breaking member may be configured to at least transport an object in the lumen of the elongated member. For example, the breaking member may be disposed in a fixed range of the elongated member on the distal side.

In addition, the structure and placement of each portion or member of the medical device shown in the embodiment may be changed as appropriate, and the optional member described with reference to drawings may be omitted or other optional members may be used as appropriate.

The detailed description above describes to a medical device. The invention is not limited, however, to the precise embodiments and variations described. Various changes, modifications and equivalents can be effected by one skilled in the art without departing from the spirit and scope of the invention as defined in the accompanying claims. It is expressly intended that all such changes, modifications and equivalents which fall within the scope of the claims are embraced by the claims.

What is claimed is:

1. A medical device for transporting an object that exists in a body lumen, the medical device comprising:
   an elongated member having a lumen extending in an axial direction;
   an insertion member inserted in the lumen of the elongated member on a distal side of the lumen, and wherein the insertion member is only partially inserted in the lumen of the elongated member; and
   a breaking member fixed on an inner surface of the elongated member such that a gap is formed between the insertion member and the breaking member in the lumen of the elongated member on the distal side, and wherein the breaking member exerts a shearing force to the object by rotating relative to the insertion member while the object is between the insertion member and the breaking member.

2. The medical device according to claim 1, wherein a distal portion of the breaking member is bent in a predetermined direction.

3. The medical device according to claim 1, wherein a distal end of the distal portion of the breaking member tapers to a point.

4. The medical device according to claim 1, wherein the breaking member is a helically extending plate-shaped member.

5. The medical device according to claim 1, wherein the distal portion of the breaking member has a cross-sectional shape that is non-circular.

6. The medical device according to claim 5, wherein the distal portion of the breaking member has a convex shape toward a center side of a rotational direction of the breaking member rather than a circumferential direction side along the rotational direction.

7. The medical device according to claim 1, wherein the breaking member extends over a predetermined range from a distal side of the lumen to a proximal side of the lumen.

8. The medical device according to claim 1, further comprising:
   a rotating body that rotates along with rotation of the elongated member on a distal portion of the elongated member;
   the insertion member being configured in a non-rotational state such that the insertion member does not rotate in conjunction with the rotation of the elongated member; and
   the breaking member is fixed to the elongated member and/or the rotating body, and the breaking member is configured to rotate along with the rotation of the elongated member.

9. The medical device according to claim 8, wherein the rotating body has a cutting unit configured to apply a cutting force with rotation of the rotating body.

10. The medical device according to claim 1, wherein a distal portion of the insertion member is a plate-shaped member.

11. The medical device according to claim 10, wherein the distal portion of the insertion member has a cross-sectional shape along a direction orthogonal to the axial direction, and wherein the cross-sectional shape is curved in a crescent shape.

12. The medical device according to claim 1, wherein a cross-sectional shape of the insertion member along a direction orthogonal to the axial direction is non-circular.

13. The medical device according to claim 1, further comprising:
a covering member;
the elongated member configured to accommodate the covering member; and
wherein the insertion member is connected to the covering member.

14. The medical device according to claim 13, wherein the insertion member includes a distal member and a proximal member, and the covering member connects the distal member of the insertion member, a distal portion of a connection member, and a proximal portion of a guide wire insertion portion to each other.

15. A medical device for transporting an object that exists in a body lumen, the medical device comprising:
an elongated member having a lumen extending in an axial direction;
a rotating body that rotates along with rotation of the elongated member on a distal portion of the elongated member;
an insertion member partially inserted in the lumen of the elongated member on a distal side of the lumen, the insertion member being configured in a non-rotational state such that the insertion member does not rotate in conjunction with the rotation of the elongated member; and
a breaking member fixed on an inner surface of the elongated member and which forms a gap between the insertion member and the breaking member in the lumen of the elongated member on the distal side, and wherein the breaking member exerts a shearing force to the object by rotating relative to the insertion member while the object is between the insertion member and the breaking member, the breaking member being fixed to the elongated member and/or the rotating body, and wherein the breaking member is configured to rotate along with the rotation of the elongated member.

16. The medical device according to claim 15, wherein a distal portion of the insertion member is a plate-shaped member, and the distal portion of the insertion member has a cross-sectional shape along a direction orthogonal to the axial direction, and wherein the cross-sectional shape is curved in a crescent shape.

17. The medical device according to claim 16, wherein the distal portion includes a plurality of groove portions configured to allow an inside of the crescent shaped distal portion to communicate with an outside of the of the crescent shaped distal portion.

18. A method for exerting a shearing force to an object from a stenosed site in a body lumen, the method comprising:
inserting a medical device into the body lumen, the medical device including an elongated member having a lumen extending in an axial direction, an insertion member inserted in the lumen of the elongated member on a distal side of the lumen, and a breaking member fixed on an inner surface of the elongated member such that a gap is formed between the insertion member and the breaking member in the lumen of the elongated member on the distal side; and
exerting a shearing force to the object by rotating the breaking member relative to the insertion member while the object is in the gap between the insertion member and the breaking member in the lumen of the elongated member on the distal side;
separating the object of the stenosed site in the body lumen by exerting tension to the part of the stenosed site with a part of the stenosed site in the gap between the insertion member and the breaking member; and
exerting a cutting force to the stenosed site via a cutting unit on a distal portion of the elongated member.

19. The method according to claim 18, further comprising:
exerting a shearing force in a state where the part of the stenosed site is hooked with a claw-like portion formed in a distal portion of the breaking member; and/or
exerting a cutting force to the part of the stenosed site with a distal end of the distal portion of the breaking member, the distal end tapering to a point.

20. The method according to claim 18, further comprising:
transporting the object, which is broken and/or severed in a state of being sandwiched in the gap between the insertion member and the breaking member to a proximal side of the elongated member via a plurality of gaps formed between the insertion member and the breaking member; and/or
after removing the medical device from the living body, transporting debris stored inside the elongated member in a distal direction to discharge to a distal side of the breaking member by driving the breaking member in a rotational direction opposite to a direction when cutting the stenosed site.

* * * * *